United States Patent
Bartholomew et al.

(10) Patent No.: US 9,816,978 B2
(45) Date of Patent: Nov. 14, 2017

(54) APPARATUS FOR ANALYSIS OF CONCRETE INCLUDING A REINFORCING BAR

(75) Inventors: Paul David Bartholomew, Springville, UT (US); William Spencer Guthrie, Provo, UT (US); Brian Anthony Mazzeo, Provo, UT (US)

(73) Assignee: Brigham Young University, Provo, UT (US)

( * ) Notice: Subject to any disclaimer, the term of this patent is extended or adjusted under 35 U.S.C. 154(b) by 220 days.

(21) Appl. No.: 13/183,300

(22) Filed: Jul. 14, 2011

(65) Prior Publication Data

US 2012/0012470 A1 Jan. 19, 2012

Related U.S. Application Data

(60) Provisional application No. 61/399,641, filed on Jul. 15, 2010.

(51) Int. Cl.
*G01N 33/38* (2006.01)

(52) U.S. Cl.
CPC .................................. *G01N 33/383* (2013.01)

(58) Field of Classification Search
CPC .......................... G01N 17/0204; G01N 33/383
USPC ...... 204/404; 205/775.5, 776.5, 77.5; 13/404
See application file for complete search history.

(56) References Cited

U.S. PATENT DOCUMENTS

| | | | |
|---|---|---|---|
| 4,401,548 A * | 8/1983 | Brezinski | 204/435 |
| 4,861,453 A * | 8/1989 | Matsuoka et al. | 204/404 |
| 5,069,774 A * | 12/1991 | Hladky et al. | 204/404 |
| 5,259,944 A * | 11/1993 | Feliu et al. | 204/404 |
| 5,370,776 A | 12/1994 | Chen | |
| 5,425,867 A | 6/1995 | Dawson et al. | |
| 5,666,061 A | 9/1997 | Assenheim | |
| 5,674,375 A * | 10/1997 | Thompson | G01N 17/02 205/724 |
| 5,792,337 A * | 8/1998 | Padovani et al. | 205/775.5 |
| 5,895,843 A | 4/1999 | Taylor et al. | |
| 6,151,969 A | 11/2000 | Miller et al. | |
| 6,805,788 B1 * | 10/2004 | Gonzalez-Martin et al. | 205/775.5 |
| 7,088,115 B1 | 8/2006 | Glenn et al. | |
| 7,466,149 B1 * | 12/2008 | Yang | 324/700 |
| 2002/0190729 A1 | 12/2002 | Wilson | |

(Continued)

FOREIGN PATENT DOCUMENTS

JP 2002286623 A 10/2002

OTHER PUBLICATIONS

Bulu Pradhan, B. Bhattacharjee, Performance evaluation of rebar in chloride contaminated concrete by corrosion rate, Construction and Building Materials, vol. 23, Issue 6, Jun. 2009, pp. 2346-2356, ISSN 0950-0618.*

(Continued)

*Primary Examiner* — Louis Rufo
(74) *Attorney, Agent, or Firm* — Brake Hughes Bellermann LLP

(57) ABSTRACT

In one general aspect, a system can include a probe configured to be coupled to a concrete surface of a portion of concrete. The system can include a waveform generator configured to trigger flow of a current to the portion of concrete via the probe and configured to reference a potential of a reinforcing bar embedded within the concrete. The system can also include a current detector configured to detect a magnitude of the current.

24 Claims, 9 Drawing Sheets

(56) References Cited

U.S. PATENT DOCUMENTS

| | | |
|---|---|---|
| 2005/0211570 A1 | 9/2005 | Jovancicevic |
| 2007/0229095 A1 | 10/2007 | Ramgopal |
| 2010/0045311 A1 | 2/2010 | Chung |

OTHER PUBLICATIONS

D.W. Law, S.G. Millard, J.H. Bungey, Linear polarisation resistance measurements using a potentiostatically controlled guard ring, NDT & E International, vol. 33, Issue 1, Jan. 2000, pp. 15-21.*

S. Feliu, J. A. González, M. L. Escudero, S. Feliu, M. C. Andrade, Possibilities of the Guard Ring for Electrical Signal Confinement in the Polarization Measurements of Reinforcements, Corrosion. 1990;46(12):1015-1020. doi:http://dx.doi.org/10.5006/1.3585049.*

"Florida Method of Test for Concrete Resistivity as an Electrical Indicator of its Permeability", Designation: FM5-578, Jan. 27, 2004, pp. 1-4.

"Resistivity Meter Calibration Box", CNS Farnell Limited, Resistivity Measurement in Concrete, 2005 (Copyright),1 page.

"RM MK II Concrete Resistivity Metter Model U95", CNS Farnell Limited, RM Concrete Resistivity Meter Operating Manual, Operating Instructions, 2008 (Copyright), pp. 1-16.

"RM-8000 Resistivity Meter", NDT James Instruments Inc., Instruction Manual, 5 pages.

"VersaSTAT 3 Hardware Manual", 30 pages.

Ewins, A. J., "Resistivity Measurements in Concrete", British Journal of NDT, vol. 32, No. 03, Mar. 1990, pp. 120-126.

Kessler, R. J., et al., "Resistivity Measurements of Water Saturated Concrete as an Indicator of Permeability", Corrosion, Corrosion Research Paper # 000553, 2005, pp. 1-10.

Millard, S. G., "Reinforced Concrete Resistivity Measurement Techniques", Structural and Building Board, Paper 9674, Proc. Instn. Civ. Engrs., Part 2, vol. 91, 1991, pp. 71-88.

Millard, S. G., et al., "Measurements of the Electrical Resistivity of Reinforced Concrete Structures for the Assessment of Corrosion Risk", British Journal NDT, vol. 31, No. 11, Nov. 1989, pp. 617-621.

Millard, S. G., et al., "Practical Measurement of Concrete Resistivity", British Journal of NDT, Resistivity Paper, vol. 33, No. 02, Feb. 1991, pp. 59-63.

International Search Report and Written Opinion received for PCT Patent Application No. PCT/US2011/044180, dated Feb. 3, 2012, 10 pages.

International Search Report and Written Opinion for International Application No. PCT/US2011/44180, dated Feb. 3, 2012, 14 pages.

* cited by examiner

APPARATUS FOR ANALYSIS OF CONCRETE INCLUDING A REINFORCING BAR

RELATED APPLICATION

This application claims priority to and the benefit of U.S. Provisional Patent Application Ser. No. 61/399,641, filed on Jul. 15, 2010, entitled, "Corrosion Analysis for Rebar Installed in Concrete," which is incorporated herein by reference in its entirety.

TECHNICAL FIELD

This description relates to methods and apparatus for analysis of concrete.

BACKGROUND

Corrosion of reinforcing steel in reinforced concrete structures (e.g., concrete parking garages, reinforced slabs on grade, concrete retaining walls, concrete buildings) is a pressing problem affecting hundreds of thousands of concrete structures such as concrete bridges. For example, the United States Federal Highway Administration has estimated that a relatively large portion (e.g., 15%) of the hundreds of thousands of bridges in the United States have been structurally compromised due to corrosion. The cost to repair or replace these highway bridges is estimated to be billions of dollars. Corrosion can be caused by, for example, chloride ions introduced to the surface of a concrete bridge deck when de-icing salts are applied to melt snow and remove ice from the area. The decision to, for example, repair or replace these concrete bridges depends largely on the corrosion state of the reinforcing bars installed within the concrete bridges and on assessments of the condition of the concrete cover over the reinforcement.

Using known techniques, assessing the condition of the concrete cover over reinforcing bars within concrete structures cannot be performed in a desirable fashion. For example, destructive, invasive methods can be used to physically examine the internal state of the concrete structure and measure the chloride content. However, these techniques may be undesirable in some situations because they require the destruction of portions of the structure. Known acoustic methods and ground penetrating radar methods can provide information about delamination and geometrical changes within the concrete, but these are generally late-stage corrosion indicators. Electrochemical methods, such as half-cell potential measurements and linear polarization, give information about the instantaneous probability and rate of reinforcement corrosion within the structure, but these known electrochemical methods do not provide direct information about the condition of the concrete cover. Concrete resistivity methods require precise conditions (e.g., precise solutions) and/or procedures to be performed with success and may not have desirable accuracy and/or coverage. In addition, some known instruments may only work in a laboratory setting where the reinforcing bars can be isolated from earth ground. In a field setting on, for example, a bridge deck, the electrical network of the bridge may be coupled to the earth ground, and, consequently, current monitoring using known instruments can yield questionable results. Thus, a need exists for systems, methods, and apparatus to address the shortfalls of present technology and to provide other new and innovative features.

SUMMARY

In one general aspect, a system can include a probe configured to be coupled to a concrete surface of a portion of concrete. The system can include a waveform generator configured to trigger flow of a current to the portion of concrete via the probe and configured to reference a potential of a reinforcing bar embedded within the concrete. The system can also include a current detector configured to detect a magnitude of the current.

In another general aspect, a computer-readable storage medium can be configured to store instructions that when executed cause a processor to perform a process. The instructions comprising instructions to trigger flow of an alternating current having a waveform defining a range of frequencies from a waveform generator to a reinforcing bar embedded within concrete via a probe coupled to a surface of the concrete, and receive an indicator of a time-resolved current magnitude of the alternating current through a portion of the concrete associated with the surface of the concrete.

In yet another general aspect, a method can include coupling a ground node of a concrete analyzer to a reinforcing bar embedded within concrete, and placing a probe over a portion of the concrete. The method can also include producing an alternating current having a waveform defining a range of frequencies through the probe.

The details of one or more implementations are set forth in the accompanying drawings and the description below. Other features will be apparent from the description and drawings, and from the claims.

DETAILED DESCRIPTION

Figure 1:
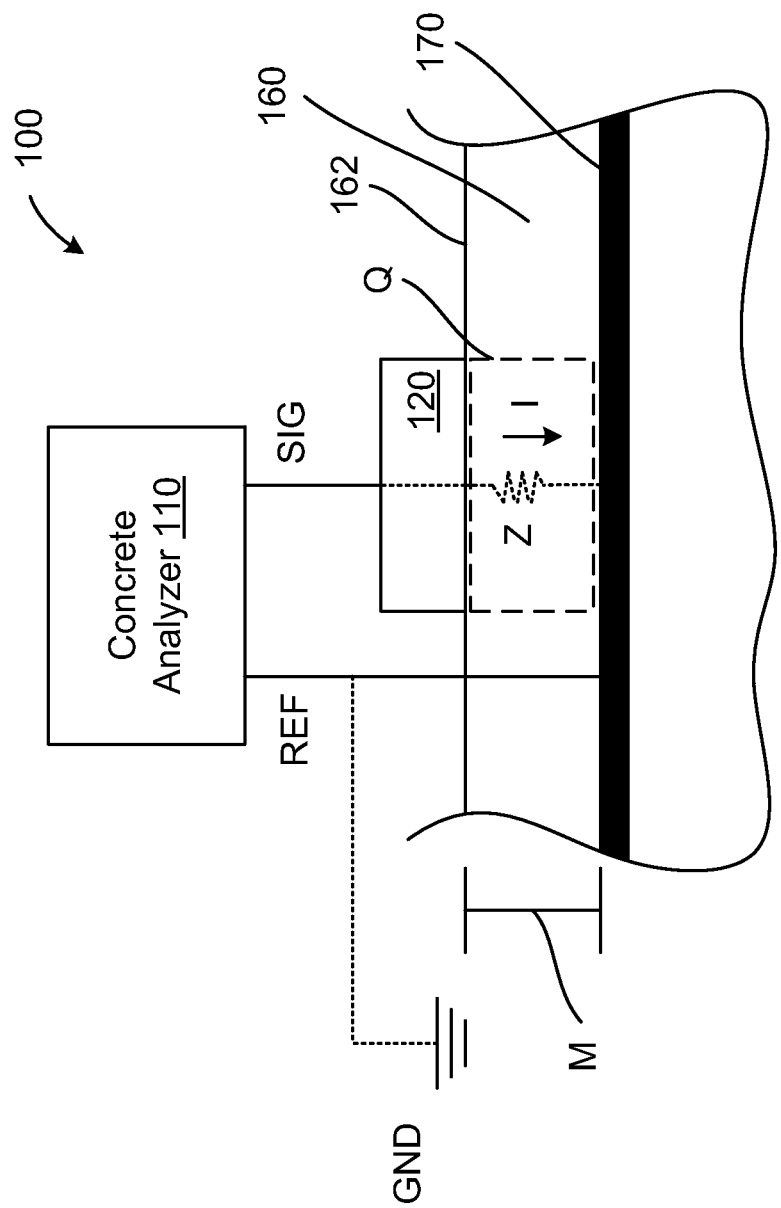
FIG. 1 is a diagram that illustrates a concrete analysis system, according to an embodiment.

FIG. 1 is a diagram that illustrates a concrete analysis system 100. As shown in FIG. 1, the concrete analysis system 100 includes a concrete analyzer 110 and a probe 120. The probe 120 is configured to be coupled to a surface 162 of concrete 160 that includes a reinforcing bar 170 installed within (e.g., embedded within) the concrete 160. The probe 120 is electrically coupled to a signal node SIG of the concrete analyzer 110. The reinforcing bar 170 and the concrete analyzer 110 are electrically coupled to a common ground represented as ground node GND. Accordingly, the concrete analyzer 110 is grounded to the reinforcing bar 170. Although not shown, in some embodiments, the reinforcing bar 170 and the concrete analyzer 110 can be coupled to a common reference that is separate from the ground node GND. In some embodiments, the concrete analysis system 100 can reference a potential of the reinforcing bar 170 which can function as a reference potential and/or as a ground. In some embodiments, the concrete analysis system 100 can be referred to as a concrete cover analysis system.

The concrete analysis system 100 is configured to determine (e.g., calculate, detect, measure) an impedance Z of a region Q of the concrete 160 using impedance spectroscopy techniques. In some embodiments, the region Q can be referred to as a target analysis region. As shown in FIG. 1, the region Q, which can represent a volume, is approximately disposed between the surface 162 of the concrete 160 and the reinforcing bar 170 in a cover portion of the concrete 162 having a thickness M. The region Q is an approximate representation of a volume of the concrete 160 for which the impedance Z is determined (e.g., calculated). In some embodiments, the impedance Z of the concrete 160 within the region Q can be approximated by the concrete analysis system 100.

The concrete analyzer 110 is configured to induce (e.g., inject, cause flow of) a current I (e.g., an instantaneous current, a maximum current, an average current, a root mean square (rms) current) in the region Q (from the signal node SIG). Based on the current I and based on the voltage drop between the signal node SIG and the reference node REF, the impedance Z of the region Q of the concrete 160 can be calculated (e.g., calculated by the concrete analyzer 110). In some embodiments, the concrete 160 can be part of a concrete structure such as a concrete parking garage, a reinforced slab on grade, a concrete retaining wall, a concrete building, and so forth.

Although many of the embodiments described herein are related to the concrete analyzer 110 producing a waveform (e.g., a voltage waveform) configured to cause flow of a current in the region Q of the concrete 160, in some embodiments, the concrete analyzer 110 can be configured to instead produce (e.g., inject) a known current (e.g., a current waveform) into the region Q of the concrete 160. In such embodiments, the voltage of the concrete 160 in the region Q can be determined (e.g., measured, derived, calculated) and used to determine an impedance (instead of measuring a current in response to a known voltage waveform to determine an impedance). Accordingly, the techniques described herein can be modified for (e.g., adapted to) various current and/or voltage profiles produced by the concrete analyzer 110.

Figure 2:
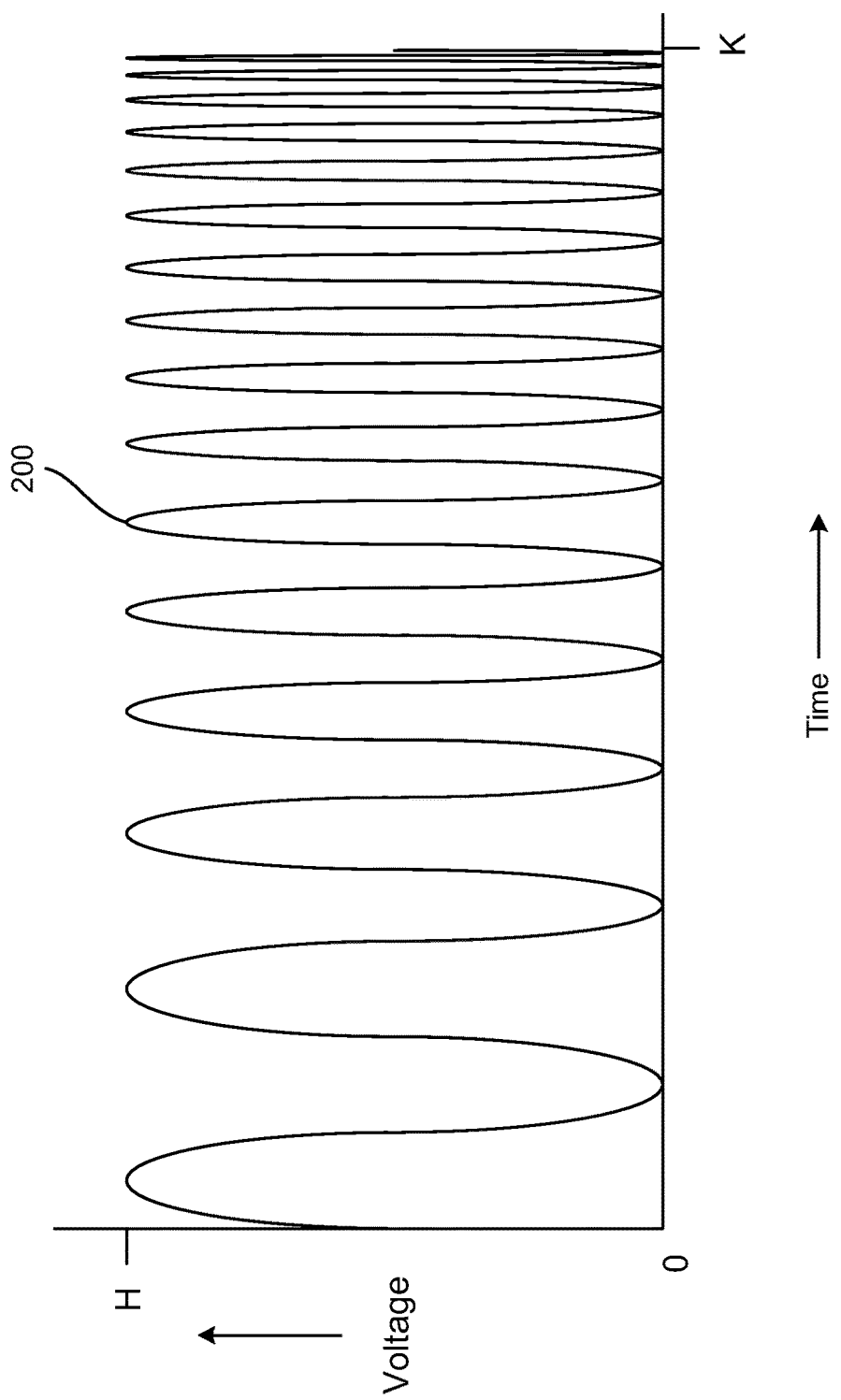
FIG. 2 is a graph that illustrates a current and voltage profile, according to an embodiment.

In some embodiments, the concrete analyzer 110 can be configured to produce a specified current and voltage profile to induce the current I in the region Q. In some embodiments, the concrete analyzer 110 can be configured to produce, for example, a signal having a specified waveform (also can be referred to as an input waveform) to induce the current I in the region Q. For example, in some embodiments, the concrete analyzer 110 can be configured to produce a sinusoidal voltage waveform (e.g., an alternating current voltage waveform) (across the signal node SIG to the reference node REF) having a fixed voltage amplitude at a specified frequency. As another example, the concrete analyzer 110 can be configured to produce a sinusoidal voltage waveform (across the signal node SIG to the reference node REF) having a fixed voltage amplitude over a range of frequencies. In some embodiments, the frequencies of the sinusoidal voltage waveform can be changed over the range of frequencies in a stepwise fashion, a continuous fashion, a random fashion, a periodic fashion, and/or so forth. An example of a sinusoidal voltage waveform 200 having a fixed voltage amplitude at voltage H over a range of frequencies that increase as time progresses to the right between time 0 and time K is shown in FIG. 2. Although not shown in FIG. 2, in some embodiments, the frequencies of the sinusoidal voltage waveform can be changed over a range of frequencies in a stepwise fashion, a continuous fashion, a random fashion, a periodic fashion, and/or so forth. In some embodiments, the waveform can also include multiple sinusoids and/or white noise superimposed to produce multiple frequency excitations simultaneously. Details related to multiple sinusoids and/or white noise are discussed below.

Referring back to FIG. 1, as yet another example related to current and/or voltage profiles, the concrete analyzer 110 can be configured to produce a constant (e.g., steady) (or substantially constant) voltage and/or constant (e.g., steady) (or substantially constant) alternating-current (AC) sinusoidal voltage waveform (across the signal node SIG to the reference node REF) having a fixed voltage amplitude at a specified frequency. In some embodiments, the concrete analyzer 110 can be configured to produce multiple signals having different profiles simultaneously, in a staggered fashion, in a specified pattern, and/or so forth. In some embodiments, the concrete analyzer 110 can be configured to produce various types of waveforms including a half-wave waveform. In some embodiments, arbitrary waveforms (e.g., square-wave waveforms, random waveforms) can be used by the concrete analyzer 110 at relatively low frequencies (e.g., at frequencies below 1 kHz or even below 100 mHz).

In some embodiments, the concrete analyzer 110 can be configured to produce a specified current and voltage profile to induce the current I in the region Q during one or more measurement cycles. For example, the concrete analyzer 110 can be configured to produce a specified current and voltage profile to induce the current I in the region Q during a first measurement cycle when the probe 120 is placed in the location shown in FIG. 1, and can be configured to produce the same current and voltage profile (or a different current and voltage profile) to induce a current in another region (not shown) during a second measurement cycle when the probe 120 is placed at another location (not shown) on the surface 162 of the concrete 160. More details related to measurement cycles are described at least, for example, in connection with FIG. 3.

The impedance Z of the region Q of the concrete 160 as determined (e.g., calculated, measured) by the concrete analyzer 160 can vary based on a variety of characteristics (e.g., concrete characteristics, concrete attributes) of the concrete 160 including, for example, chloride concentration in the region Q, the thickness M of the concrete cover, coatings (e.g., epoxy coatings) that may be present on the reinforcing bar 170, the quality of the concrete 160 in the region Q (as related to porosity, tortuosity, pore interconnectivity, etc.), degree of water saturation, the temperature of (e.g., temperature profile across) the concrete 160 in the region Q, and/or so forth. Accordingly, the impedance Z of the region Q of the concrete 160 can be an indicator of one or more of the characteristics described above. The characteristics described above can be used to indirectly determine (e.g., ascertain, project) the potential corrosion state of the reinforcing bar 170. Moreover, the characteristics described above can be indicators of the ability of the concrete 160 to protect the reinforcing bar 170 from corrosion (e.g., diffusion of ions that can cause corrosion). Thus, one or more of the characteristics described above can be determined (or identified) based on one or more indicators of the impedance Z of the region Q of the concrete 160. More details related to determination of characteristics of a region of concrete based on impedance (e.g., impedance spectroscopy) are described below.

Although not shown in FIG. 1, the reinforcing bar 170 can be disposed within a plane (not shown) that is parallel to, or approximately parallel to, the surface 162 of the concrete 160. In some embodiments, the reinforcing bar 170 can be part of a mat or a mesh (e.g., a relatively planar mat or mesh) of reinforcing bars embedded within the concrete 160 so that the concrete is reinforced concrete.

Figure 3:
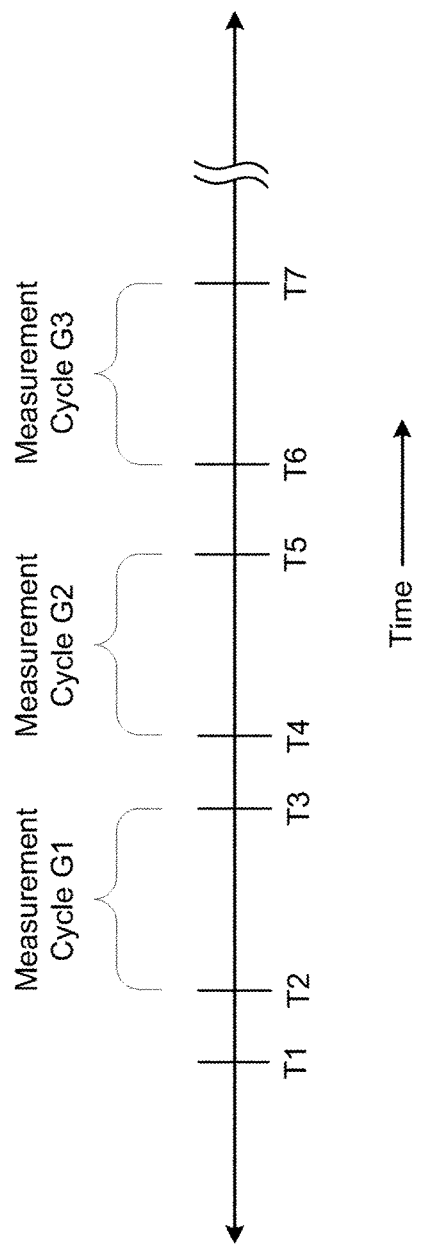
FIG. 3 is a timeline that illustrates use of the concrete analysis system shown in FIG. 1, according to an embodiment.

FIG. 3 is a timeline that illustrates use of the concrete analysis system 100 shown in FIG. 1, according to an embodiment. In this embodiment, the concrete analysis system 100 is grounded to the ground node GND approximately at time T1. During each of the measurement cycles G1 through G3, the concrete analysis system 100 can be configured to produce a specified current and voltage profile to induce the current in various regions of the concrete 160 (e.g., current I in region Q of the concrete 160). Accordingly, impedance measurements can be obtained during each measurement cycles G1 through G3 by the concrete analysis system 100. In some embodiments, for example, the concrete analyzer 110 can be configured to produce a signal having a specified and/or a different waveform (e.g., input waveform) during each of the measurement cycles G1 through G3.

In this embodiment, each of the measurement cycles G1 through G3 is associated with a different location on the surface 162 of concrete 160. Specifically, between time T1 and time T2, the probe 120 can be placed at a first location on the surface 162 of the concrete 160 and, starting at time T2, the measurement cycle G1 can be commenced (e.g., triggered). After the measurement cycle G1 has been completed at time T3, the probe 120 can be moved from the first location to a second location on the surface 162 of the concrete 160. In some embodiments, the first location (or area or region associated with the first location) can overlap with the second location (or area or region associated with the second location), or can be mutually exclusive from the second location. While the probe is at the second location, the measurement cycle G2 can be performed between times T4 and T5. Similarly, after the measurement cycle G2 has been completed at time T5, the probe 120 can be moved from the second location to a third location on the surface 162 of the concrete 160. In some embodiments, the second location (or area or region associated with the first location) can overlap with the third location (or area or region associated with the second location), or can be mutually exclusive from the third location. While the probe is at the third location, the measurement cycle G3 can be performed between times T6 and T7. In another embodiment (not shown) multiple probes can be used simultaneously to perform measurements at multiple locations.

In this embodiment, the grounding of the concrete analysis system 100 performed approximately at time T1 can remain intact (e.g., may not be moved) during each of the measurement cycles G1 through G3. In other words, the concrete analysis system 100 remains grounded at the same location during each of the measurement cycles G1 through G3 even though the probe 120 is moved between the measurement cycles G1 through G3. Thus, grounding of the concrete analysis system 100 may not be separately performed for each of the measurement cycles G1 through G3. Although three separate measurement cycles are shown in FIG. 3, in some embodiments, more than 3 measurement cycles, or less than 3 measurement cycles can be associated with a single ground location.

Although not shown, in some embodiments, the concrete analyzer 110 and/or the probe 120 can be configured so that the probe 120 can be continuously moved along the surface 162 of the concrete 160 and used to measure the impedance of the concrete under the probe 120 as the probe 120 is moved. In other words, impedance values can be calculated as the probe 120 is moved along the surface 162 of the concrete 160. In such embodiments, the probe 120 can be configured with a surface that can slidably move along the surface 162 of the concrete 160 and/or that can be rolled along the surface 162 of the concrete 160.

Figure 4A:
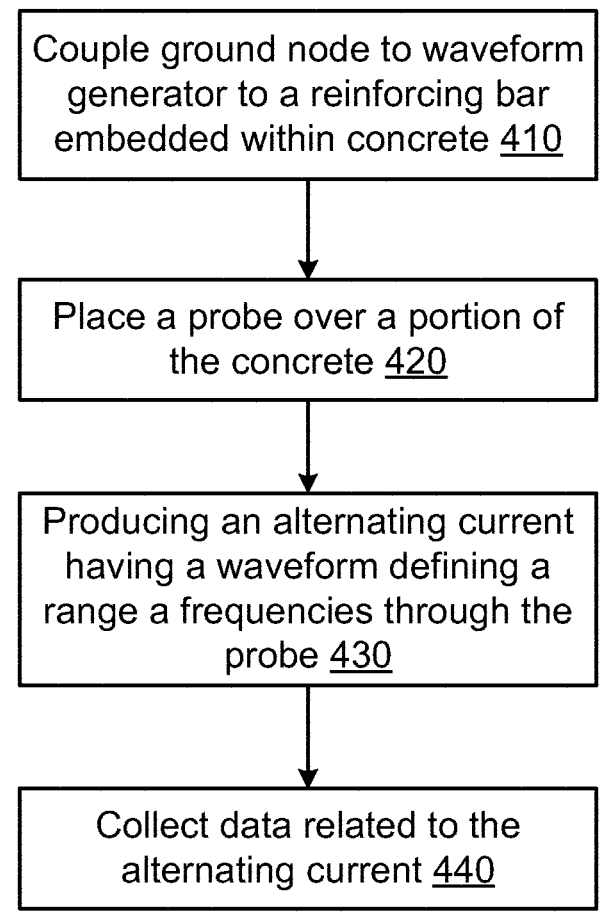
FIG. 4A is a diagram that illustrates a method for determining an impedance of a region within concrete, according to an embodiment.

FIG. 4A is a diagram that illustrates a method for determining an impedance of a region within concrete, according to an embodiment. At least some portions of the method shown in FIG. 4A can be performed using, for example, one or more portions of the concrete analysis system 100 shown in FIG. 1.

A reference node REF of a concrete analyzer is coupled to a reinforcing bar embedded within concrete (block 410). In some embodiments, the ground node of the concrete analyzer (e.g., the concrete analyzer 110 shown in FIG. 1) can be coupled to the reinforcing bar (e.g., the reinforcing bar 170 shown in FIG. 1) by drilling (using a hammer drill) a hole (e.g., a hole having a ¾-inch diameter) into concrete (e.g., concrete 160 shown in FIG. 1) around the reinforcing bar until the reinforcing bar can be contacted. In some embodiments, the ground node of the concrete analyzer can be coupled to the reinforcing bar via a stainless steel connection, a clip, a screw-fit connection, a press-fit connection, and/or so forth.

A probe is placed over a portion of the concrete (block 420). In some embodiments, a fluid (e.g., water, an ionic solution, detergent in water) can be applied to at least a portion of the probe and/or the concrete surface (e.g., the probe 120 shown in FIG. 1) before the probe is placed over (e.g., contacted with) the portion of the concrete. In some embodiments, the probe and/or the concrete surface can be saturated with the fluid before the probe is placed over a portion of concrete. The fluid can be configured to facilitate transfer of electrical signals (e.g., current and/or voltage signals) between the probe and the concrete. In other words, the fluid can define a conductive interface between the electrical probe and the concrete (which can include an ionic compound). The fluid can function as a transitional medium between the electrical probe and the concrete.

In some embodiments, the probe 120 can be configured, for example, with steel wool or other compressible material that can be coupled to a concrete surface in a desirable fashion so that application of a fluid may not be required. In other words, the probe 120 can be configured so that the probe 120 can be coupled to a concrete surface under dry conditions.

An alternating current having a waveform (e.g., an input waveform) defining a range of frequencies through the probe is produced (block 430). The current can be triggered to flow through a region of concrete below the probe and into the reference and/or ground node using the concrete analyzer 110. For example, the concrete analyzer 110 can be configured to produce a sinusoidal voltage waveform having a fixed voltage amplitude over the range of frequencies. In some embodiments, the frequencies of the sinusoidal voltage waveform can be changed over the range of frequencies in a stepwise fashion, a continuous fashion, a random fashion, a periodic fashion, simultaneously, and/or so forth.

Data (e.g., values) related to the current are collected (block 440). In some embodiments, the data related to the current can be collected so that an impedance of the region of the concrete can be determined (e.g., calculated, measured, derived, obtained). In some embodiments, the data can include current values, voltage values (e.g., voltage values at the current values), temperature values, date/time stamp information, location information (e.g., related to a location of the probe on the concrete), and/or so forth.

In some embodiments, the portion of the concrete (in block 420) can be a first portion of the concrete and the producing (in block 430) can include producing a first alternating current starting at a first time. The method can also include placing a probe over a second portion of the concrete separate from the first portion of the concrete while the ground node of the concrete analyzer remains coupled to the reinforcing bar embedded within the concrete, and producing, starting at a second time, a second alternating current through the probe and through the second portion of the concrete. In some embodiments, the first alternating current and the second alternating current may be associated with different measurement cycles.

In some embodiments, one or more measurement cycles (e.g., measurement cycles G1 through G3 shown in FIG. 3) can include a waveform with multiple frequencies applied simultaneously (e.g., concurrently). In other words, a waveform including two or more frequencies (can be referred to a multi-frequency waveform) applied simultaneously can be produced using a concrete analyzer (e.g., concrete analyzer 110). A graph of multiple frequencies applied simultaneously is shown in FIG. 4B.

Figure 4B:
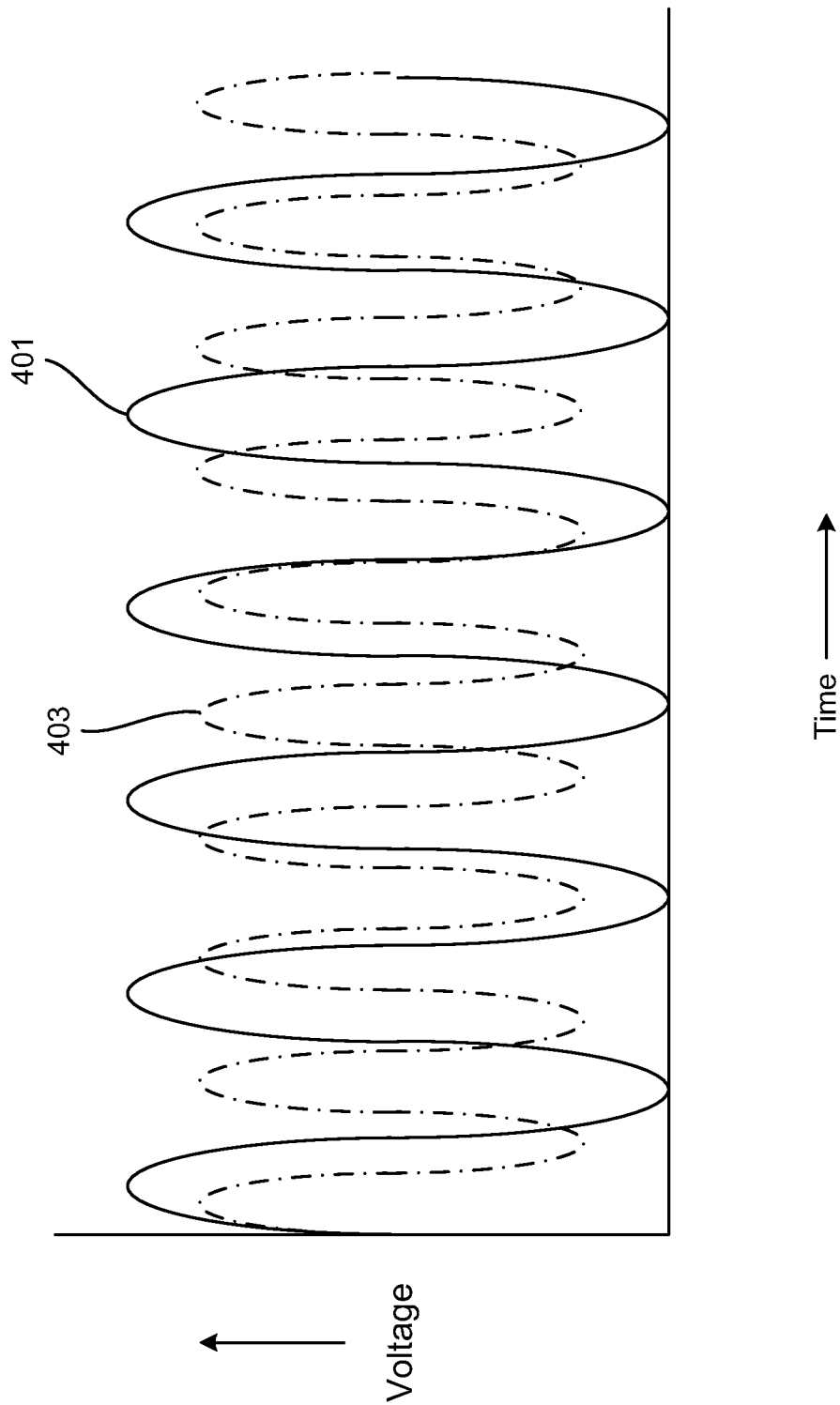
FIG. 4B is graph of multi-frequency waveform, according to an embodiment.

As shown in FIG. 4B, a first portion 401 of a waveform has a first amplitude and has a first frequency, and a second portion 403 of the waveform has a second amplitude different from the first amplitude and has a second frequency that is different from the first frequency. In some embodiments, the portions 401, 403 can be referred to as waveform components. In some embodiments, a waveform can have more than two simultaneous portions, more than two frequencies (e.g., frequencies that vary over time), varying amplitudes, and/or so forth. In some embodiments, the portions 401, 403 can each be individually referred to as waveforms that collectively define a multi-frequency waveform. In some embodiments, a waveform having multiple (e.g., two) simultaneously applied frequencies can be represented, for example, by the following formula: $Y(t)=\sin(\omega_A \cdot t) + \sin(\omega_B \cdot t)$.

In a scenario where a multi-frequency waveform is produced and used by a concrete analyzer (e.g., concrete analyzer 110), data (e.g., current data, voltage data) related to the multi-frequency waveform can be logged. The current induced within concrete in response to the multi-frequency waveform can be analyzed using a mathematical analysis (e.g., a transform analysis) such as a Fourier analysis (e.g., a Fourier Transform analysis (e.g., a Fast Fourier Transform analysis), a wavelet analysis), a Hilbert analysis, and/or so forth. Using such techniques the current data (e.g., current values) at each of the frequencies associated with the multi-frequency waveform can be resolved (e.g., separated out). In other words, through post processing of the current data (e.g., time-resolved current magnitudes) can be used to separate out current associated with each of the frequency components using Fourier analysis. By applying multiple frequencies in a waveform simultaneously in a parallel fashion, a duration of a measurement cycle can be reduced compared with a duration of a measurement cycle where frequencies of a waveform are applied in a serial fashion.

In some embodiments, one or more of a pulse, a square wave, and so forth can be applied to a concrete sample using a concrete analyzer. In some embodiments, the pulse, the square wave, and/or so forth can be a collection of sinusoids. Such waveform types can induce a response similar that of applying a multi-frequency waveform, and can be analyzed using Fourier analysis. The results of, for example, a square wave can be similar to the results obtained from a multi-frequency waveform.

In some embodiments, one or more measurement cycles (e.g., measurement cycles G1 through G3 shown in FIG. 3) can include a waveform based on a stochastic process. For example, the waveform can be white noise or shaped noise defined (e.g., produced) based on a stochastic process. In a scenario where the waveform is a white noise waveform produced and used by a concrete analyzer (e.g., concrete analyzer 110), data (e.g., current data, voltage data) related to the white noise waveform can be logged. The current induced within concrete in response to the white noise waveform can be analyzed using, for example, Fourier analysis (e.g., a Fourier Transform analysis (e.g., a Fast Fourier Transform analysis), a wavelet analysis). The auto-correlation can be computed from a current induced within concrete by the white noise waveform. Fourier transformation of the autocorrelation function can be performed to yield the power spectral density of the stochastic process. The underlying impedance of the concrete can then be derived (e.g., inferred) from the power spectral density or mathematical transformation.

Figure 5:
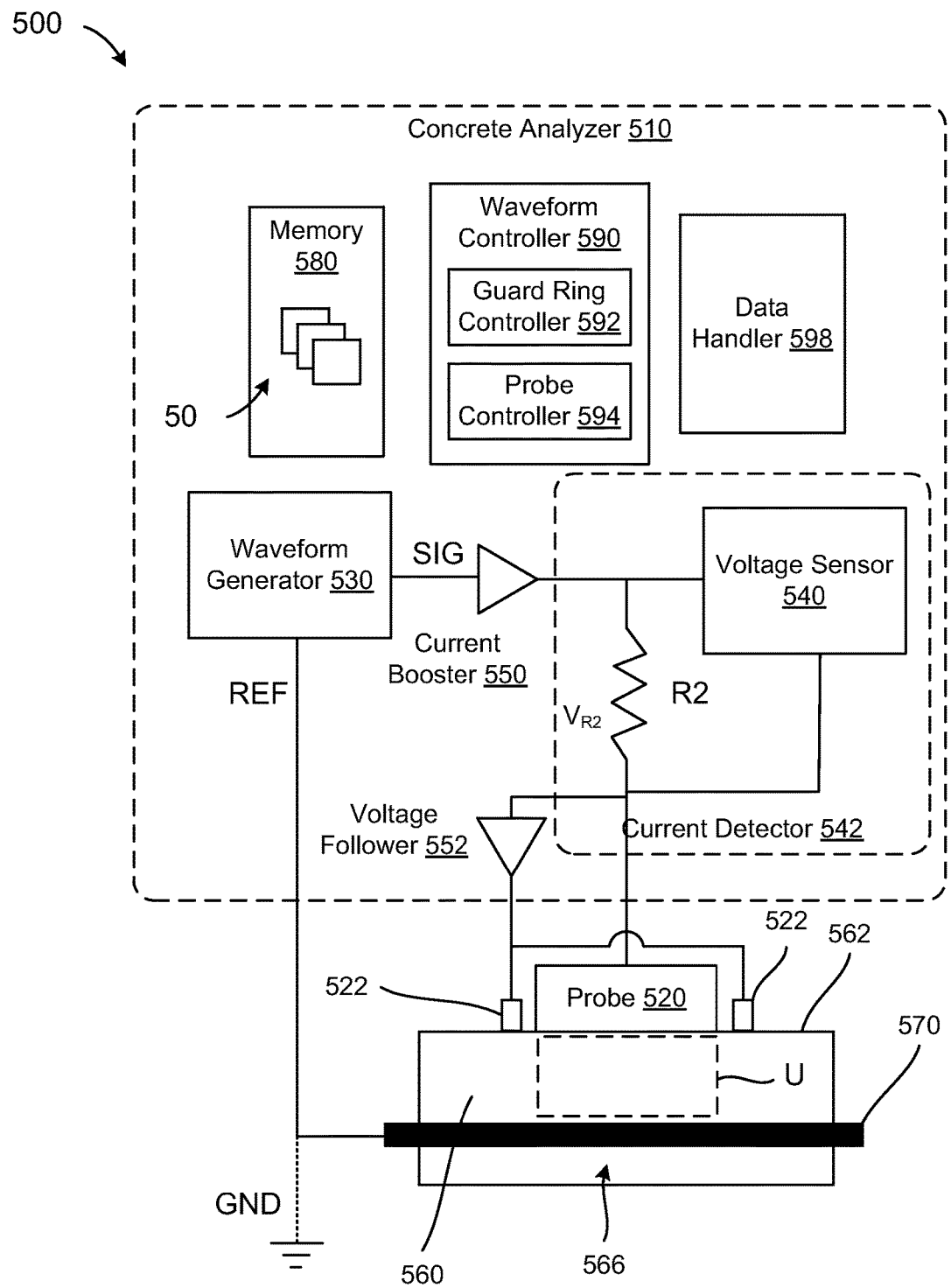
FIG. 5 is a diagram that illustrates another concrete analysis system, according to an embodiment.

FIG. 5 is a diagram that illustrates another concrete analysis system 500, according to an embodiment. As shown in FIG. 5, the concrete analysis system 500 includes a concrete analyzer 510 and a probe 520. The probe 520 is configured to be coupled to a surface 562 of concrete 560 that includes a reinforcing bar 570 (installed within (e.g., embedded within) the concrete 560 using impedance spectroscopy techniques. The probe 520 is electrically coupled to a signal node SIG of the concrete analyzer 510. The reinforcing bar 570 and the concrete analyzer 510 are electrically coupled to a common ground, which can be represented as ground node GND. Accordingly, the concrete analyzer 510 is grounded to the reinforcing bar 570. Although not shown, in some embodiments, the reinforcing bar 570 and the concrete analyzer 510 can be coupled to a common reference that is separate from the ground node GND. The concrete analysis system 500 is configured to determine (e.g., calculate, approximately determine, measure) an impedance of a region U of the concrete 560. In some embodiments, the probe 520 may or may not be disposed directly over (e.g., vertically over) the reinforcing bar 570 during a measurement cycle. In other embodiments, the probe 520 may be disposed directly over multiple reinforcing bars.

The concrete analyzer 510 includes a waveform generator 530 configured to induce (e.g., inject, cause flow of) a current in the region U (from the signal node SIG). Based on the current and based on the voltage drop between the signal node SIG and the reference node REF, the impedance of the region U of the concrete 560 can be calculated (e.g., calculated by the concrete analyzer 510).

In some embodiments, the waveform generator 530 is configured to produce a specified current and voltage profile to induce the current in the region U based on one or more waveform profiles 50 (e.g., input waveform profiles 50) (during one or more measurement cycles) stored in a memory 580 of the concrete analyzer 510. In some embodiments, the waveform profiles 50 can collectively be referred to as a library of waveform profiles. In some embodiments, the waveform generator 530 can be controlled (e.g., triggered), at least in part, by a waveform controller 590 of the concrete analyzer 510. Specifically, the waveform generator 530 can include a probe controller 594 configured to trigger the waveform generator 530 to cause a current and/or voltage profile to be induced within the region U via the probe 520. In some embodiments, the waveform controller 590 (or portions thereof) can be integrated into the waveform generator 530.

In some embodiments, the waveform generator 530 can be any type of waveform generator such as an Agilent Waveform Generator 33250A. In some embodiments, the waveform generator 530 can be a relatively low output impedance waveform generator.

In some embodiments, one or more of the waveform profiles 50 can be configured to cause the waveform generator 530 to produce a sinusoidal voltage waveform (e.g., an alternating current voltage waveform) (across the signal node SIG to the reference node REF) having a fixed voltage amplitude at a specified frequency. As another example, one or more of the waveform profiles 50 can be configured to cause the waveform generator 530 to produce a sinusoidal voltage waveform (across the signal node SIG to the reference node REF) having a fixed or varying (e.g., changing) voltage amplitude over a range of frequencies.

As shown in FIG. 5, a guard ring 522 is disposed around the probe 520. In some embodiments, the guard ring 522 can be considered a component of the probe 520. The guard ring 522 can be configured to produce electrical potential that confines (e.g., substantially confines, limits) a measurement current and a voltage through the probe 520 to the region U. In other words, current spreading in the measurement can be limited. In some embodiments, the guard ring 522 can be configured to produce an electrical potential that is approximately equal to an electrical potential of the probe 520 so that a current and/or voltage associated with the probe 520 may not extend (e.g., extend laterally) beyond a perimeter of the guard ring 522 (if projected into the concrete 560. Accordingly, current and voltage produced in response to one or more of the waveform profiles 50 through the probe 520 can be limited to the region U by the guard ring 522. In some embodiments, the guard ring 522 can be configured to have electrical potential that causes the region U to be smaller or larger or a different shape than that shown in FIG. 5.

As shown in FIG. 5, the guard ring 522 is electrically coupled to the signal node SIG. Guard ring 522 can be electrically coupled to the signal node SIG so that an electrical potential of the guard ring 522 may be substantially the same as an electrical potential of the probe 520. Moreover, the electrical potential of the guard ring 522 will change with the electrical potential of a waveform induced at the probe 520.

The guard ring 522 is electrically coupled to the signal node SIG via a voltage follower 552. In some embodiments, the voltage follower 552 can be a buffer amplifier configured to decrease (or eliminate) loading effects. In some embodiments, the voltage follower 552 can be configured to isolate the guard ring 522 signal node SIG so that current and/or voltage from the waveform generator 530 to the probe 520 may not be disturbed by the guard ring 522. In some embodiments, the voltage follower 552 can be configured to provide a current to the guard ring 522.

Although not shown in FIG. 5, in some embodiments, the voltage follower 552 optionally may be omitted from the concrete analysis system 500. In some embodiments, the guard ring 522 (e.g., an electrical potential of the guard ring 522), a current through the guard ring 522) can be controlled by a guard ring controller 592 of the waveform controller 590. In some embodiments, the guard ring 522 can be controlled by a guard ring controller 592 of the waveform controller 590 via the voltage follower 552.

As shown in FIG. 5, the waveform generator 530 can be coupled to a current booster 550. The current booster 550 can be configured to amplify a current produced by the waveform generator 530 because the concrete 560 can have a relatively high impedance input. In some embodiments, the current booster 550 can be configured to increase current produced by the waveform generator 530 so that a voltage produced by the waveform generator 530 can be maintained at a voltage triggered by one or more of the waveform profiles 50. In some embodiments, the current booster 550 can have a unity gain implemented using a feedback signal. In some embodiments, the current booster 500 can be configured to match an output impedance of the waveform generator 530 with an input impedance of the current booster 550. This can ensure that a form (e.g., an amplitude, a frequency, etc.) of the output waveform of the waveform generator 530 is applied precisely to the concrete 560 in a form that matches the form of the output waveform. Thus, if you have a varying impedance load, the linearity and power transfer of the waveform generator 530 to the concrete 560 will be desirable.

Although not shown in FIG. 5, in some embodiments, the current booster 550 optionally may be omitted from the current analysis system 500. In some embodiments, a voltage amplifier can be used in conjunction with, or instead of, the current booster 550. In some embodiments, the current booster 550, or a portion thereof, can be controlled by the probe controller 594 of the waveform controller 590.

As shown in FIG. 5, a resistor R2 is electrically coupled between the current booster 550 and the probe 520. A voltage $V_{R2}$ across the resistor R2 can be measured by a voltage sensor 540 of the concrete analyzer 510. In some embodiments, the voltage sensor 540 can be, for example, a multimeter (e.g., an Agilent multimeter). The voltage $V_{R2}$ across resistor R2 can be used to determine (e.g., detect, calculate) a current flowing into region U of the concrete 560 via the probe 520. For example, based on the known resistance of resistor R2 and a measured voltage $V_{R2}$ across the resistor R2, a current into the probe 520 (and guard ring 522) can be determined (e.g., calculated). In some embodiments, a resistance of the resistor R2 can be smaller (e.g., 10 times smaller, 100 times smaller) than, greater than, or approximately equal to an impedance of the region U of the concrete 560. In some embodiments, the voltage sensor 540 and resistor R2 can collectively function as a current detector 542.

In the embodiment shown in FIG. 5, the concrete analyzer 110 produces a waveform (e.g., a voltage waveform) configured to cause flow of a current in the region U of the concrete 560. Although not shown, in some embodiments, the concrete analyzer 510 can be configured to instead produce (e.g., inject) a known current (e.g., a current waveform) into the region U of the concrete 560. In such embodiments, the voltage of the concrete 560 across the region U can be determined (e.g., measured, derived, calculated) using a voltage detector (not shown) and used to determine an impedance (instead of measuring a current in response to a known voltage waveform to determine an impedance). In such embodiments, the voltage detector can be configured to measure a voltage between the reference node REF and the signal node SIG, and the measured voltage can be used in conjunction with the known injected current to calculate (e.g., derive) an impedance.

The concrete analyzer 510 includes a data handler 598 configured to handle the data associated with the concrete analyzer 510. For example, the data handler 598 can be configured to log (e.g., store) voltage values produced by the voltage sensor 540, log current and/or voltage values associated with the waveform generator 530, and/or so forth. In some embodiments, the data handler 598 can be configured to store one or more values in the memory 580. In some embodiments, the data handler 598 can include, or can be based on, a variety of programs and/or interfaces including, for example, LabVIEW.

In some embodiments, voltage values measured by the voltage sensor 540 and/or logged by the data handler 598 can vary depending on one or more of the waveform profiles 50 applied to the probe 520. For example, for a frequency sweep from a few milli-Hertz (e.g., 100 mHz) to several hundred Hertz (e.g., 200 Hz), the voltage sensor 540 can be configured to measure voltage in a direct-current (DC) coupling mode, and the number of values logged by the data handler 598 can increase (or decrease) as the frequency increases (e.g., log values at 0.06-second intervals when the frequency is below 1 Hz, log values at 0.006-second intervals for frequencies between 1 Hz and 10 Hz, log values at 0.0001-second intervals for frequencies between 10 Hz and 200 Hz). For relatively high frequencies (e.g., 200 Hz to 1 MHz) the voltage sensor 540 can be configured to measure voltage in an alternating current (AC) coupling mode. Similarly, the number of values logged by the data handler 598 can be increased (or decreased) as the frequency increases.

In some embodiments, for relatively low-frequency analysis (e.g., for analysis up to 100 Hz, for analysis up to 1 kHz), the amplitude of, for example, sinusoidal signals associated with one or more waveforms applied to the probe 520 can be extracted. In some embodiments, curve-fitting methods (e.g., non-linear curve fitting methods), such as the application of the least-squares curve fit (lsqcurvefit) (which is a non-linear curve fit) function in MATLAB can be used to approximate (e.g., extract) a sinusoidal signal. These functions can be used to approximate the amplitude of the sinusoid at the set frequency from voltages (e.g., potentials) logged by the data handler 598. In some embodiments, magnitude data (e.g., magnitude values) and phase data (e.g., phase values) can also be obtained. In some embodiments, the magnitude values can also be fit again (e.g., fit again using non-linear curve fitting functions) for parameter extraction of the overall shape of the curves. As a specific example, the lsqcurvefit function can be used to fit the data to, for example, the following function: $M/(1+(j\omega\tau)\alpha)^{\beta}+R_c$ where M is the magnitude of the relaxation, $\tau$ is the time constant of the relaxation, $\alpha$ and $\beta$ are Cole-Cole parameters describing the asymmetry and logarithmic slope of the relaxation, and $R_c$ is the baseline resistance of the measured impedance. In some embodiments, the base 10 logarithm of the impedance can be used, as well as exponential quantities for the relaxation magnitude, time constant, and baseline resistance. In some embodiments, approximated amplitudes can be used to calculate current passing through the concrete 560 within region U into the grounded reinforcing bar 570, and/or can be used to, for example, determine the impedance of the interface between at least a portion of the concrete 560 and reinforcing bar 570.

In some embodiments, one or more of the components of the concrete analysis system 510 can be integrated into a single device or a mobile (e.g., movable) device. For example, the probe 520, the waveform generator 530, the voltage sensor 540, the data handler 598, the waveform controller 590, and/or the memory 580 can be included in a movable cart, or other type of apparatus, that can be used to move the concrete analysis system 500 on, for example, a bridge deck, a building roof, a concrete walkway, and/or so forth. Accordingly, the concrete analysis system 510 can be used to determine the impedance of various locations of the concrete structure.

In some embodiments, one or more of the waveform profiles 50 can be selected for use during one or more measurement cycles. For example, a first waveform profile from the waveform profiles 50 can be selected for use during a first measurement cycle, and a second waveform profile from waveform profiles 50 can be selected for use during a second measurement cycle. In some embodiments, the first waveform can be a direct current (DC) voltage applied (e.g., applied in discrete voltage levels and/or current levels) to the probe 520, and the second wave form can include an alternating-current (AC) sinusoidal voltage waveform (across the signal node SIG to the reference node REF) having a fixed voltage amplitude at a specified frequency. In some embodiments, one or more of the waveform profiles 50 can be selected for use during consecutive measurement cycles. In some implementations, one or more of the waveform profiles 50 can be defined by (e.g., customized by) a user of the concrete analysis system 500. In some implementations, the concrete analysis system 500 can be configured to use a default waveform profile.

In some embodiments, one or more of the waveform profiles 50 can be defined and/or used based on a concrete type, specified environmental conditions, and/or so forth. For example, a waveform profile from the waveform profiles 50 can be used by the concrete analysis system 500 for concrete that has a specified characteristic (e.g., a specified age, concrete installed in a particular geographic region or pattern, concrete experiencing certain conditions over a period of time).

In some implementations, at least one or more portions of the concrete analysis system 500 can be configured to operate at a host device (e.g., through a host device, function within a host device). In such implementations, the concrete analysis system 500 can be accessed through a network by a client device (e.g., a laptop computer), which can function as a client to a host device where at least some portions of the concrete analysis system 500 are operating. Accordingly, the functionality of the concrete analysis system 500 can be called and/or executed on an on-demand basis. In some implementations, at least some portions of the concrete analysis system 500 such as the waveform controller 590 and/or the data handler 598 can function as a background application. In some implementations, at least some portions of the concrete analysis system 500 can function as an application (or service) that can be accessed via an application programming interface (API).

The concrete analysis system 500 can be, or can include, any type of hardware and/or software configured to analyze the concrete 560. In some implementations, one or more portions of the components shown in the concrete analysis system 500 in FIG. 5 can be, or can include, a hardware-based module (e.g., a digital signal processor (DSP), a field programmable gate array (FPGA), a memory), a firmware module, and/or a software-based module (e.g., a module of computer code, a set of computer-readable instructions that can be executed at a computer). For example, in some implementations, one or more portions of the concrete analysis system 500 can be, or can include, a software module configured for execution by at least one processor (not shown). In some implementations, the functionality of the components can be included in different modules and/or different components than those shown in FIG. 5. For example, although not shown, the functionality of the waveform controller 590 of the concrete analysis system 500 can be included in a different module of the concrete analysis system 500, or divided into several different modules.

Although not shown, in some implementations, the concrete analysis system 500 (or portions thereof) can be configured to operate within, for example, a data center (e.g., a cloud computing environment), a computer system, one or more server/host devices, and/or so forth. In some implementations, the concrete analysis system 500 (or portions thereof) can be configured to operate within a network. Thus, the concrete analyzer 510 (or portions thereof) can be configured to function within various types of network environments that can include one or more client devices and/or one or more server devices. For example, the network can be, or can include, a local area network (LAN), a wide area network (WAN), and/or so forth. The network can be, or can include, a wireless network and/or wireless network implemented using, for example, gateway devices, bridges, switches, and/or so forth. The network can include one or more segments and/or can have portions based on various protocols such as Internet Protocol (IP) and/or a proprietary protocol. The network can include at least a portion of the Internet.

The concrete analysis system 500 can be configured to operate based on one or more platforms (e.g., one or more similar or different platforms) that can include one or more types of hardware, software, firmware, operating systems, runtime libraries, and/or so forth. In some implementations, the concrete analysis system 500 (or a portion thereof) can represent a cluster of devices (e.g., a server farm). In such an implementation, the functionality and processing of the concrete analysis system 500 (or a portion thereof) can be distributed to several devices of the cluster of devices.

Although not shown, in some implementations, the memory 580 can be implemented as more than one memory component (e.g., more than one random-access memory (RAM) component or disk drive memory) associated with the concrete analysis system 500. In some implementations, the memory 580 can be a database memory. In some implementations, the memory 580 can be, or can include, a non-local memory. For example, the memory 580 can be, or can include, a memory shared by multiple devices (not shown). In some implementations, the memory 580 can be associated with a server device (not shown) within a network and configured to serve the concrete analysis system 500.

Figure 6A:
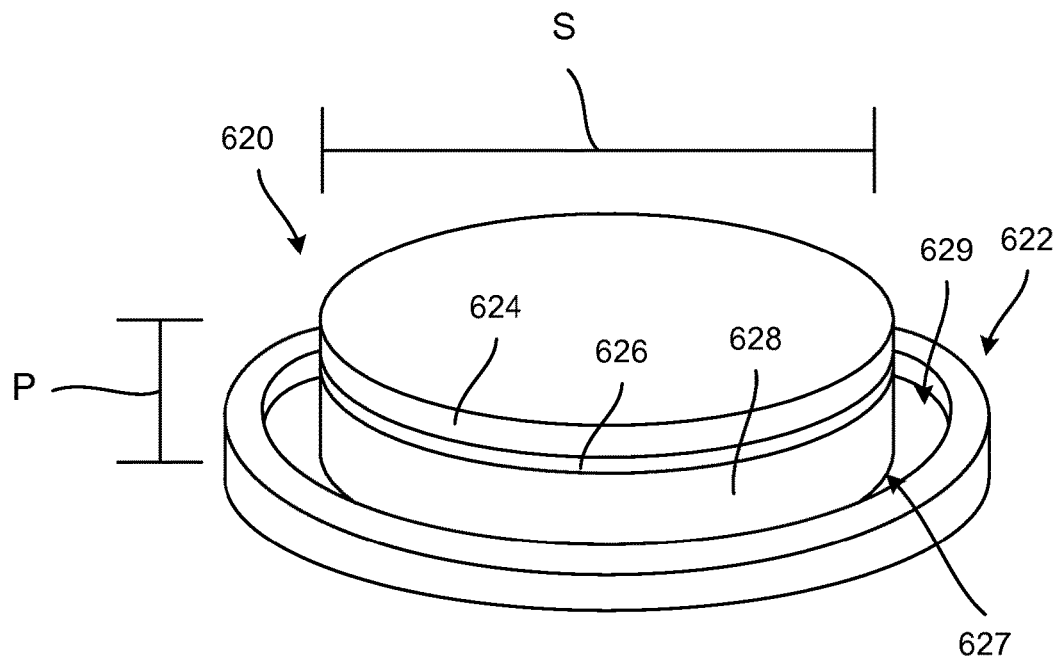
FIGS. 6A and 6B are diagrams that illustrate a probe and a guard ring, according to an embodiment.
Figure 6B:
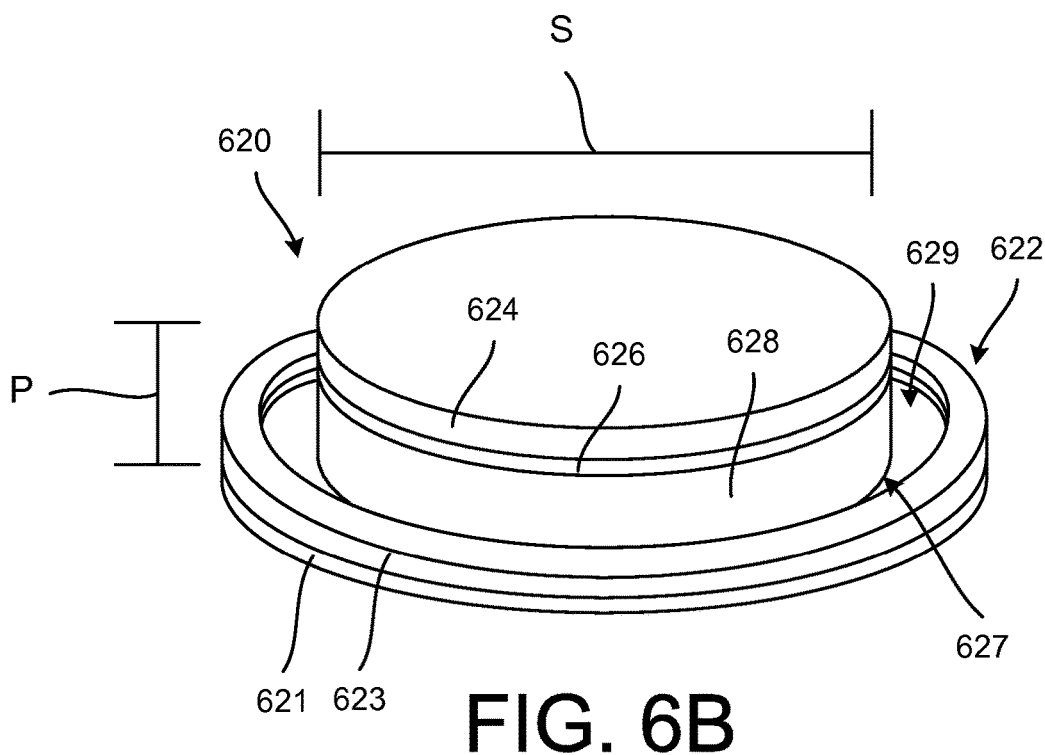

FIGS. 6A and 6B are diagrams that illustrate a probe 620 and a guard ring 622, according to an embodiment. As shown in FIGS. 6A and 6B, the probe 620 includes multiple layers of material. Specifically, the probe 620 includes a conductive portion 626 disposed between a fluid retention portion 628 and a support portion 624. The conductive portion 626 can be made of a variety of conductive materials such as aluminum, copper, steel wool, stainless steel, a conductive epoxy, and/or so forth. The fluid retention portion 628 can be made of any type of material that can be configured to retain a conductive fluid such as an ionic solution (e.g., a solution with a detergent, a salt solution). In some embodiments, the fluid retention portion 628 can be made of, for example, Styrofoam (e.g., compressible Styrofoam), wood, a sponge (e.g., a stiff sponge), and so forth. The guard ring 622 can be made of a variety of conductive materials such as aluminum, copper, steel wool, stainless steel, and/or so forth. In some embodiments, the guard ring 622 can have the same layers (e.g., conductive portion, support portion, fluid retention portion) or different layers than the probe 620. For example, as shown in FIG. 6B, the guard ring 622 includes a fluid retention portion 621 and a conductive portion 623. Although not shown in FIG. 6B, the guard ring 622 can also include a support portion. Referring back to FIGS. 6A and 6B, in some embodiments, the support portion 624 can be made of, for example, a plastic material, an insulating material, and/or so forth. In some embodiments, the support portion 624 may be optionally omitted from the probe 620.

In some embodiments, the probe 620 can include layers in addition to those shown in FIGS. 6A and 6B. For example, in some embodiments, the probe 620 can include multiple conductive portions (or layers) and/or multiple fluid retention portions (or layers).

In some embodiments, the fluid retention portion 628 can have a bottom surface 627 configured to contact a surface of a portion of concrete (not shown). In some embodiments, the bottom surface 627 of the fluid retention portion 628 can be configured to conform, at least in part, to a surface of concrete. Accordingly, the fluid retention portion 628 can be made of a flexible (or semi-flexible) material that can enable a relatively stable electrical contact between the probe 620 and a concrete surface. In some embodiments, the bottom surface 627 of the fluid retention portion 628 can be configured so that it is rigid and does not conform, at least in part, to a surface of concrete. In some embodiments, the probe 620 can be a compressible probe.

As shown in FIGS. 6A and 6B, a gap 629 is between the guard ring 622 and the probe 620. In some embodiments, the gap 629 can be a fraction of the a diameter S of the probe 620. For example, the gap 629 can be less than or equal to $1/10$ of the diameter S of the probe 620, or greater than $1/10$ of the diameter S of the probe 620. In some embodiments, the gap 629 between the guard ring 622 and the probe 620 can be uniform or can be non-uniform. In some embodiments, one or more materials can be inserted in the gap 629 between the guard ring 622 and the probe 620 to function as an insulator between the guard ring 622 and the probe 620.

As shown in FIGS. 6A and 6B, the probe 620 has a circular shape or outer profile. The probe 620 has the diameter S of approximately 15 centimeters (cm). In some embodiments, the diameter S of the probe 620 can be different than 15 cm. For example, the probe 620 can have a diameter S of approximately 100 cm. In some embodiments, the probe 620 can have a diameter S greater than 100 cm or a diameter S less than or equal to 100 cm.

In some embodiments, reinforcing bars within concrete can define a grid (or some other pattern). In some embodiments, the probe 620 can be configured with a footprint (e.g., bottom surface area) that spans multiple reinforcing bars. In other words, in some embodiments, the probe 620 can be configured with a footprint that is greater than a grid size defined by reinforcing bars installed within concrete. The probe 620 can be configured to span multiple reinforcing bars so that current can more easily flow from the probe 620 through the concrete to the reinforcing bars, which define a ground node relative to the probe 620.

In some embodiments, the footprint of the probe 620 (e.g., the bottom surface 627 of the probe 620) can be approximately 100 cm². In some embodiments, the footprint of the probe 620 can be greater than 100 cm² or less than 100 cm².

In some embodiments, the probe 620 can have a variety of shapes. For example, the probe 620 can have a square outer profile, a rectangular outer profile, an octagonal outer profile, and so forth. In some embodiments, the bottom surface 627 of the probe 620 may not be flat (e.g., may be curved).

As shown in FIGS. 6A and 6B, probe 620 has a thickness P. In some embodiments, the thickness P of the probe 620 can be several centimeters. For example, the probe 620 can have a thickness P of approximately 5 cm. In some embodiments, the probe 620 can have a thickness P greater than 5 cm or a thickness P less than or equal to 5 cm.

In some embodiments, one or more weight elements can be placed on, or included in, the probe 620 to facilitate contact of the probe 620 with the surface of the concrete. In other words, in some embodiments, a weight element can be integrated into the probe 620. In some embodiments, other types of mechanical mechanisms can be used to facilitate contact of the probe 620 with a concrete surface. For example, a mechanical clip or other type of relatively sticky substance can be used to facilitate relatively tight contact of the probe 620 with the concrete surface.

Figure 7:
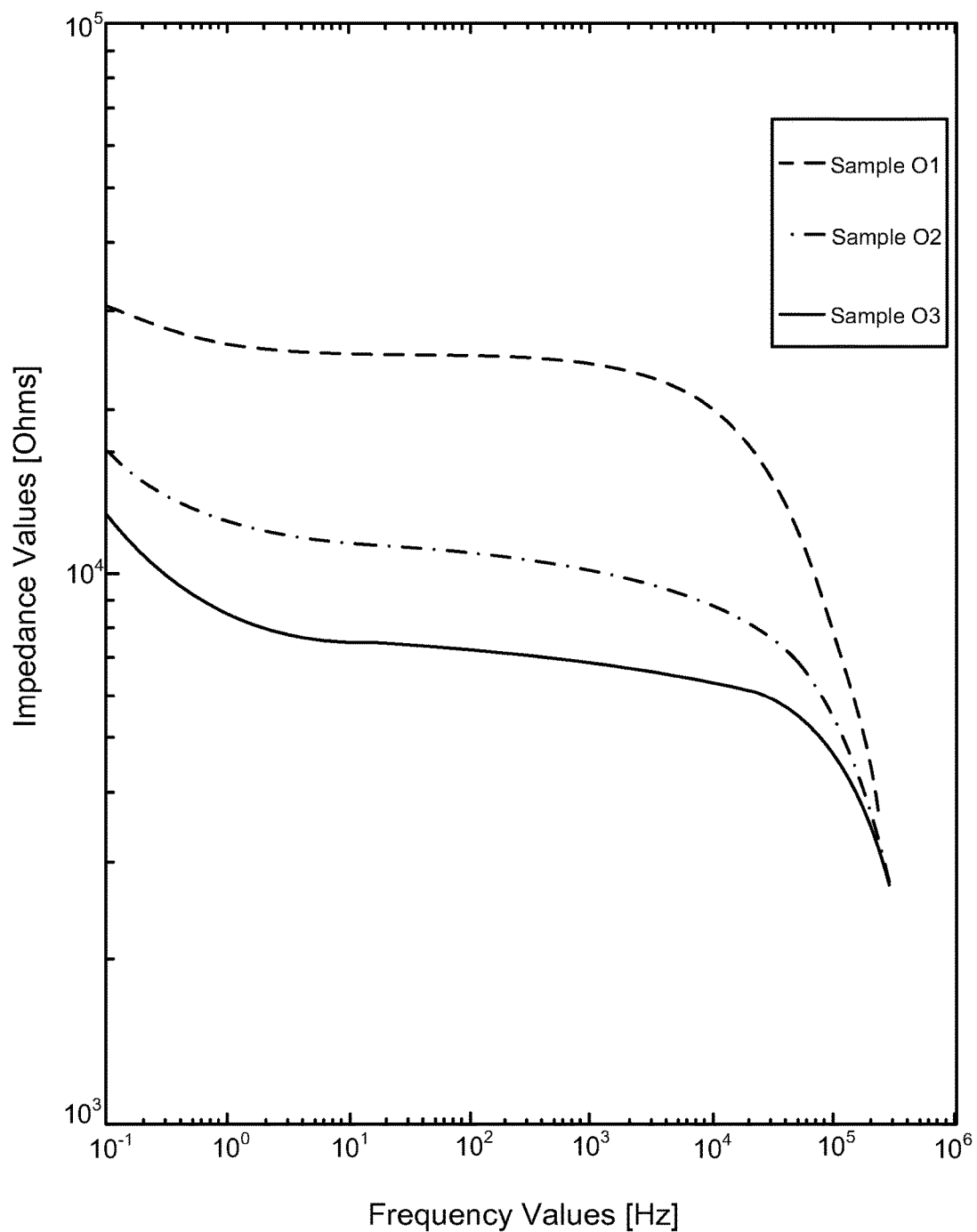
FIG. 7 is a graph that illustrates impedance values related to several concrete samples versus frequency values of an input waveform, according to an embodiment.

FIG. 7 is a graph that illustrates impedance values related to three concrete samples versus frequency values of an input waveform, according to an embodiment. The input waveform can be similar to the input waveform frequency sweep shown in FIG. 2. Impedance values (in ohms) are shown along the y-axis, and frequency values (in hertz) are shown along the x-axis.

Sample O1 does not include any chlorides, while samples O2 and O3 include chloride concentrations of 10 pounds per cubic yard of concrete (0.593 kg/cubic meter). Samples O1 and O2 both have a water-cement ratio of 0.40, while sample O3 has a water-cement ratio of 0.60. Each of the samples O1 through O3 has approximately the same cover thickness above a reinforcing bar.

As shown in FIG. 7, the impedance spectroscopy techniques described herein can produce different curves that can be used to identify different characteristics of the samples. Specifically, sample O1, which does not include chloride ions and has the lower water-cement ratio, has the highest impedance over the entire frequency range. Sample O3, which includes chloride ions and has the higher water-cement ratio, has the lowest impedance over the entire frequency range. In this embodiment, the lines do not intersect, and the characteristics of the concrete samples can be derived from the impedance values over the entire frequency range. Although not shown in FIG. 7, various other characteristics can be determined (e.g., calculated) using the techniques described herein.

As shown in FIG. 7, the impedance values of each of the samples decreases as the frequency values increase. In some embodiments, the shapes of the curves can be caused by changes in polarization interactions as the frequency values change.

Figure 8:
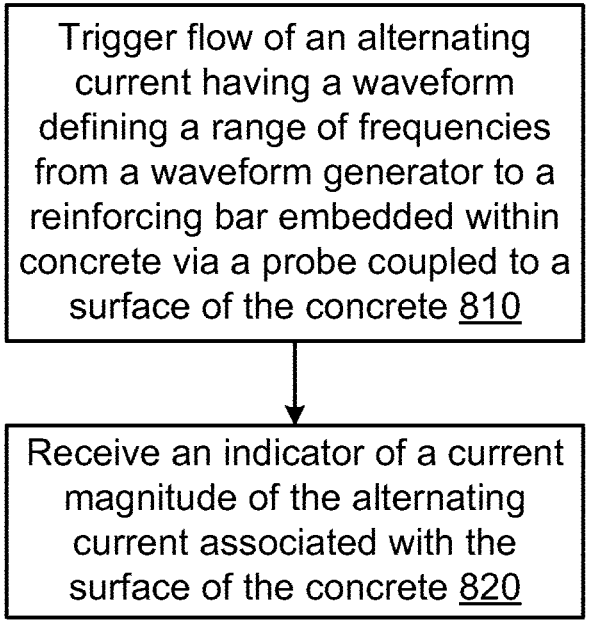
FIG. 8 is a diagram that illustrates another method for determining an impedance of a region within concrete, according to an embodiment.

FIG. 8 is a diagram that illustrates another method for determining an impedance of a region within concrete, according to an embodiment. At least some portions of the method shown in FIG. 8 can be performed using, for example, one or more portions of the concrete analysis system 100 shown in FIG. 1 and/or the concrete analysis system 500 shown in FIG. 5.

Flow of an alternating current having a waveform defining a range of frequencies from a waveform generator to a reinforcing bar embedded within concrete is triggered via a probe coupled to a surface of the concrete (block 810). In some embodiments, the waveform can be triggered by the waveform controller 590 using the waveform generator 530. In some embodiments, the waveform can be triggered based on one or more of the waveform profiles 50 stored in the memory 580 shown in FIG. 5.

An indicator of a current magnitude of the alternating current associated with the surface of the concrete is received (block 820). In some embodiments, the current magnitude of the alternating current is measured via a resistor (e.g., resistor R2) and by a voltage sensor (e.g., voltage sensor 540). In some embodiments, the data handler 598 can be configured to log (e.g., store) data associated with the current magnitude of the alternating current. Other methods such as induction (instead of, or in conjunction with resistor R2), feedback associated with current booster 550, etc. could be used to measure the time-varying current.

Implementations of the various techniques described herein may be implemented in digital electronic circuitry, or in computer hardware, firmware, software, or in combinations of them. Implementations may implemented as a computer program product (e.g., a computer program tangibly embodied in an information carrier, a machine-readable storage device, a computer-readable medium, a tangible computer-readable medium) for processing by, or to control the operation of, data processing apparatus, e.g., a programmable processor, a computer, or multiple computers. In some implementations, a tangible computer-readable storage medium can be configured to store instructions that when executed cause a processor to perform a process. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be processed on one computer or on multiple computers at one site or distributed across multiple sites and interconnected by a communication network.

Method steps may be performed by one or more programmable processors executing a computer program to perform functions by operating on input data and generating output. Method steps also may be performed by, and an apparatus may be implemented as, special-purpose logic circuitry (e.g., an FPGA (field programmable gate array) or an ASIC (application-specific integrated circuit)).

Processors suitable for the processing of a computer program include, by way of example, both general and special-purpose microprocessors, and any one or more processors of any kind of digital computer. Generally, a processor will receive instructions and data from a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data (e.g., magnetic, magneto-optical disks, or optical disks). Information carriers suitable for embodying computer program instructions and data include all forms of non-volatile memory, including by way of example semiconductor memory devices (e.g., EPROM, EEPROM, and flash memory devices; magnetic disks (e.g., internal hard disks or removable disks); magneto-optical disks; and CD- ROM and DVD-ROM disks. The processor and the memory may be supplemented by, or incorporated in special-purpose logic circuitry.

To provide for interaction with a user, implementations may be implemented on a computer having a display device (e.g., a cathode ray tube (CRT), a light emitting diode (LED), or liquid crystal display (LCD) display device) for displaying information to the user and a keyboard and a pointing device, e.g., a mouse or a trackball, by which the user can provide input to the computer. Other kinds of devices can be used to provide for interaction with a user, as well; for example, feedback provided to the user can be any form of sensory feedback (e.g., visual feedback, auditory feedback, or tactile feedback); and input from the user can be received in any form, including acoustic, speech, or tactile input.

Implementations may be implemented in a computing system that includes a back-end component (e.g., as a data server), or that includes a middleware component (e.g., an application server), or that includes a front-end component (e.g., a client computer having a graphical user interface or a Web browser through which a user can interact with an implementation), or any combination of such back-end, middleware, or front-end components. Components may be interconnected by any form or medium of digital data communication (e.g., a communication network). Examples of communication networks include a local area network (LAN) and a wide area network (WAN) (e.g., the Internet).

While certain features of the described implementations have been illustrated as described herein, many modifications, substitutions, changes, and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components, and/or features of the different implementations described.

What is claimed is:

1. A system, comprising:
   a single probe including a first fluid retention portion having a top portion coupled to a first conductive portion and defining a bottom surface of the probe;
   a single guard ring disposed around an outside of at least a portion of the probe, the guard ring including a second fluid retention portion having a top coupled to a second conductive portion and defining a bottom surface of the guard ring, the bottom surface of the guard ring being physically separated by a gap from the bottom surface of the first fluid retention portion;
   a waveform generator;
   a current detector electrically coupled between the waveform generator and the single probe; and
   a voltage follower electrically coupled between the current detector and the guard ring.

2. The system of claim 1, wherein the probe is configured to be coupled to a concrete surface of a portion of concrete, the waveform generator is configured to trigger flow of a current to the portion of concrete via the probe and configured to reference a potential of a reinforcing bar embedded within the concrete, the current detector is configured to detect a magnitude of the current, the current is an alternating current, a frequency of the alternating current is varied over time during a single, continuous measurement cycle.

3. The system of claim 1, wherein the probe is configured to be coupled to a concrete surface of a portion of concrete, the waveform generator is configured to trigger flow of a current to the portion of concrete via the probe and configured to reference a potential of a reinforcing bar embedded within the concrete, the current detector is configured to detect a magnitude of the current, the current is associated with at least one of a multi-frequency waveform or a waveform produced based on a stochastic process.

4. The system of claim 1, wherein the probe is configured to be coupled to a concrete surface of a portion of concrete, the waveform generator is configured to trigger flow of a first current to the portion of concrete via the probe and configured to reference a potential of a reinforcing bar embedded within the concrete, the current detector is configured to detect a magnitude of the first current,
   the system further comprising:
   a resistor electrically coupled between the waveform generator and the probe, the current detector is configured to detect the magnitude of the first current through the resistor; and
   a current booster electrically coupled between the resistor and the guard ring and configured to produce a second current for the guard ring based on the first current.

5. The system of claim 1, further comprising:
   a guard ring controller configured to trigger an electrical potential at the guard ring substantially equal to an electrical potential of the probe.

6. The system of claim 1, wherein the probe is configured to be coupled to a concrete surface of a portion of concrete, the waveform generator is configured to trigger flow of a first current to the portion of concrete via the probe and configured to reference a potential of a reinforcing bar embedded within the concrete, the current detector is configured to detect a magnitude of the first current,
   the system further comprising:
   a current booster configured to produce the first current based on a second current produced by the waveform generator, the first current having a current magnitude greater than a current magnitude of the second current.

7. The system of claim 1, further comprising:
   a current booster electrically coupled between the waveform generator and the probe, the current booster configured to boost a magnitude of a current triggered by the waveform generator.

8. The system of claim 1, wherein the probe is configured to be coupled to a concrete surface of a portion of concrete, the probe has a surface configured to contact the surface of the portion of concrete, a surface area of the surface is greater than 100 square centimeters.

9. The system of claim 1, wherein the probe is configured to be coupled to a concrete surface of a portion of concrete, the waveform generator is configured to trigger flow of a current to the portion of concrete via the probe and configured to reference a potential of a reinforcing bar embedded within the concrete, the reinforcing bar embedded within the concrete functions as a ground node, at least one of the current or a voltage associated with the current has a substantially constant amplitude.

10. The system of claim 1, wherein the probe is configured to be coupled to a concrete surface of a portion of concrete, the waveform generator is configured to trigger flow of a current to the portion of concrete via the probe and configured to reference a potential of a reinforcing bar embedded within the concrete, the reinforcing bar embedded within the concrete functions as a ground node, the waveform generator is configured to vary a voltage amplitude of the current relative to the ground node during a single, continuous measurement cycle.

11. The system of claim 1, further comprising:
a resistor electrically coupled between the waveform generator and the probe; and
a voltage follower electrically coupled between the resistor and the guard ring.

12. The system of claim 1, wherein the first fluid retention is electrically separated from the second fluid retention portion.

13. The system of claim 1, wherein the gap between the probe and the guard ring is non-uniform.

14. The system of claim 1, wherein at least one of the first fluid retention portion and the second fluid retention portion includes at least one of a foam and a sponge.

15. The system of claim 1, wherein the gap includes an insulating material.

16. The system of claim 1, wherein the first conductive portion has a surface area at least equal to a surface area of the bottom surface of the probe.

17. A system, comprising:
a single probe including a first fluid retention portion defining a bottom surface of the probe;
a first conductive portion coupled to a top of the first fluid retention portion;
a single guard ring disposed around an outside of at least a portion of the probe, the guard ring including a second fluid retention portion defining a bottom surface of the guard ring;
a second conductive portion coupled to a top of the second fluid retention portion;
the bottom surface of the guard ring being physically separated from the bottom surface of the first fluid retention portion;
a waveform generator;
a voltage detector electrically coupled between the waveform generator and the single probe; and
a voltage follower electrically coupled between the voltage detector and the guard ring.

18. The system of claim 17, wherein the probe is configured to be coupled to a concrete surface of a portion of concrete, the waveform generator is configured to trigger flow of a current to the portion of concrete via the probe and configured to reference a potential of a reinforcing bar embedded within the concrete, the voltage detector is configured to detect a magnitude of a voltage across at least a portion of the concrete caused by the current, the current is an alternating current, a frequency of the alternating current is varied over time during a single, continuous measurement cycle.

19. The system of claim 17, wherein the probe is configured to be coupled to a concrete surface of a portion of concrete, the waveform generator is configured to trigger flow of a current to the portion of concrete via the probe and configured to reference a potential of a reinforcing bar embedded within the concrete, the voltage detector is configured to detect a magnitude of a voltage across at least a portion of the concrete caused by the current, the current is associated with at least one of a multi-frequency waveform or a waveform produced based on a stochastic process.

20. The system of claim 17, wherein the probe is configured to be coupled to a concrete surface of a portion of concrete, the waveform generator is configured to trigger flow of a first current to the portion of concrete via the probe and configured to reference a potential of a reinforcing bar embedded within the concrete, the voltage detector is configured to detect a magnitude of a voltage across at least a portion of the concrete caused by the first current,
the system further comprising:
a resistor electrically coupled between the waveform generator and the probe, the voltage detector is configured to detect the magnitude of the first current using the resistor; and
a current booster electrically coupled between the resistor and the guard ring and configured to produce a second current for the guard ring based on the first current.

21. The system of claim 17, further comprising:
a guard ring controller configured to trigger an electrical potential at the guard ring substantially equal to an electrical potential of the probe.

22. The system of claim 17, wherein the probe is configured to be coupled to a concrete surface of a portion of concrete, the waveform generator is configured to trigger flow of a first current to the portion of concrete via the probe and configured to reference a potential of a reinforcing bar embedded within the concrete, the voltage detector is configured to detect a magnitude of a voltage across at least a portion of the concrete caused by the first current,
the system further comprising:
a current booster configured to produce the first current based on a second current produced by the waveform generator, the first current having a current magnitude greater than a current magnitude of the second current.

23. The system of claim 17, further comprising:
a current booster electrically coupled between the waveform generator and the probe, the current booster configured to boost a magnitude of a current triggered by the waveform generator.

24. The system of claim 17, wherein the probe is configured to be coupled to a concrete surface of a portion of concrete, the waveform generator is configured to trigger flow of a current to the portion of concrete via the probe and configured to reference a potential of a reinforcing bar embedded within the concrete, the voltage detector is configured to detect a magnitude of a voltage across at least a portion of the concrete caused by the current, the reinforcing bar embedded within the concrete functions as a ground node, at least one of the current or a voltage associated with the current has a substantially constant amplitude.

* * * * *